United States Patent
Wilcox et al.

(10) Patent No.: US 6,592,814 B2
(45) Date of Patent: *Jul. 15, 2003

(54) BIOMEDICAL DEVICES WITH ANTIMICROBIAL COATINGS

(75) Inventors: Mark Wilcox, Sydney (AU); Timothy Williams, Storrs, CT (US); Rene Schneider, Campinas (BR); Douglas Vanderlaan, Jacksonville, FL (US)

(73) Assignee: Johnson & Johnson Vision Care, Inc., Jacksonville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/165,562

(22) Filed: Oct. 2, 1998

(65) Prior Publication Data

US 2002/0068013 A1 Jun. 6, 2002

(51) Int. Cl.[7] .......................... A61L 12/14; A01N 12/34
(52) U.S. Cl. ..................... 422/28; 424/411; 424/429; 514/2; 514/839
(58) Field of Search .................. 422/28; 424/411, 424/423, 429, 430, 434, 437; 514/2, 836, 839, 840

(56) References Cited

U.S. PATENT DOCUMENTS

| | | | |
|---|---|---|---|
| 4,184,849 A | 1/1980 | Cambiaso et al. | |
| 5,328,954 A | 7/1994 | Sarangapani | |
| 5,447,914 A | 9/1995 | Travis et al. | 514/16 |
| 5,472,703 A | 12/1995 | Vanderlaan et al. | 424/429 |
| 5,486,579 A * | 1/1996 | Lai et al. | 525/479 |
| 5,514,732 A | 5/1996 | Vanderlaan et al. | |
| 5,515,117 A | 5/1996 | Dziabo et al. | |
| 5,549,894 A | 8/1996 | Hunt | 424/94.64 |
| 5,607,681 A | 3/1997 | Galley et al. | |
| 5,955,316 A * | 9/1999 | Conneely et al. | 435/69.7 |

FOREIGN PATENT DOCUMENTS

| | | |
|---|---|---|
| EP | 0 050 934 | 5/1982 |
| EP | 0 372 130 | 6/1990 |
| EP | 0 604 369 | 6/1994 |
| GB | 2209523 * | 5/1989 |
| JP | 043343103 | 11/1992 |
| WO | WO 92/15198 | 9/1992 |

OTHER PUBLICATIONS

Jung, J & Rapp, J, "The Efficacy of Hydrophilic Contact Lens Cleaning Systems in Removing Protein Deposits", The Contact Lens Association of Ophthalmologists Journal, vol. 19(1), Jan. 1993 (Whole Document).

Williams, T.J. et al. Optometry and Vision Science, vol. 75(4) Apr. 4, 1998; "Interactions of bacteria with contact lenses: The effect of soluble protein and carbohydrate on bacterial adhesion to contact lenses". p 266–271. (Whole document).

Baguet, J. et al. Biomaterials, vol. 16(1), 1995: "Characterisation of lacrymal comonent accumulation on worn soft contact lens surface by atomic force microscropy". p 3–9 (Whole Document).

(List continued on next page.)

*Primary Examiner*—Elizabeth McKane

(57) ABSTRACT

Contact lenses with antimicrobial coatings are provided. One or more surfaces of the lenses are coated with lactoferrin to impart antimicrobial properties to the surface.

10 Claims, 1 Drawing Sheet

OTHER PUBLICATIONS

Leahy, C.D. et al. Optometry & Vision Science, vol. 67(7), 1990: "Initial in vivo tear protein deposition on individual hydrogel contact lenses". p 504–511. (Whole document).

Miller, M.J. et al. Journal of Clinical Microbiology, vol. 26(3), Mar. 1988: "Effects of protein, mucin, and human tears on dherence of Pseudomonas aeruginosa to hydrophillic contact lenses". p 513–517. (Whole document).

Gadmunsson, O.G. et al. Arch. Ophthalmology, vol. 103, Feb. 1985: Identification of proteins in contact lens surface deposits by immunofluorescence microscopy. p 196–197. (Whole document).

Chemical Abstracts, vol. 102, No. 16, issued Apr. 22, 1985 Columbia, Ohio, USA, Ishil, Yoshimoto; Iwata, Shuzo, "Studies on the interaction between contact lens and tear fluid (VII). Phenomenon of human tear Iysozyme and lactoferrin adsorption onto contact lens material", p. 370, column 2, the abstract No. 137743p, Nippon Kontakuto Renzu Gakkai Kaishi. 1984, 26(3), 225–9 (Japan) Abstract.

Kijlstra, A, "The Role of Lactoferrin in the Nonspecific Immune Response on the Ocular Surface", Reg. Immunol, 3(4) :Abstract, 1990–91.

Bellamy, W. et al., "Antibacterial Spectrum of Lactoferricin B, a Potent Bactericidal Peptide Derived from the N–terminal Region of Bovine Lactofferin", J. Appl. Bacteriol, 73(6):Abstract, Dec. 1992.

Tomita, M. et al., "Potent Antibacterial Peptides Generated by Pepsin Digestion of Bovine Lactoferrin", J. Dairy Sci., 74 (12) :Abstract, Dec. 1991.

Yamauchi, K. et al., "Antibacterial Activity of Lactoferrin and a Pepsin–Derived Lactoferrin Peptide Fragment", Infect Immun, 61(2) :Abstract Feb. 1993.

* cited by examiner

US 6,592,814 B2

BIOMEDICAL DEVICES WITH ANTIMICROBIAL COATINGS

FIELD OF THE INVENTION

This invention relates to coated devices. In particular, the invention provides biomedical devices on the surfaces of which antimicrobial protein coatings are formed.

BACKGROUND OF THE INVENTION

Devices for use in and on the human body are well known. The chemical composition of the surfaces of such devices plays a pivotal role in dictating the overall efficacy of the devices. Additionally, it is known that providing such devices with an antimicrobial surface is advantageous.

A wide variety of bactericidal and bacteriostatic coatings have been developed. For example, cationic antibiotics, such as polymyxin, vancomycin, and tetracycline have been used as coatings for contact lenses. Further, metal chelating agents, substituted and unsubstituted polyhydric phenols, aminophenols, alcohols, acid and amine derivatives, and quarternary ammonium have been used as antimicrobial agents for contact lenses.

However, the use of these known antimicrobial coatings has disadvantages. With the use of antibiotic coatings, microorganisms resistant to the antibiotics may develop. Chelating agent use fails to address the numbers of bacteria that adhere to the device. Some of the prior art coatings, for example phenol derivatives and cresols, can produce ocular toxicity or allergic reactions. Quarternary ammonium compounds are problematic because of their irritancy. Thus, a need exists for safe and effective antimicrobial coatings that overcomes at least some of these disadvantages.

DETAILED DESCRIPTION OF THE INVENTION AND PREFERRED EMBODIMENTS

Figure 1:
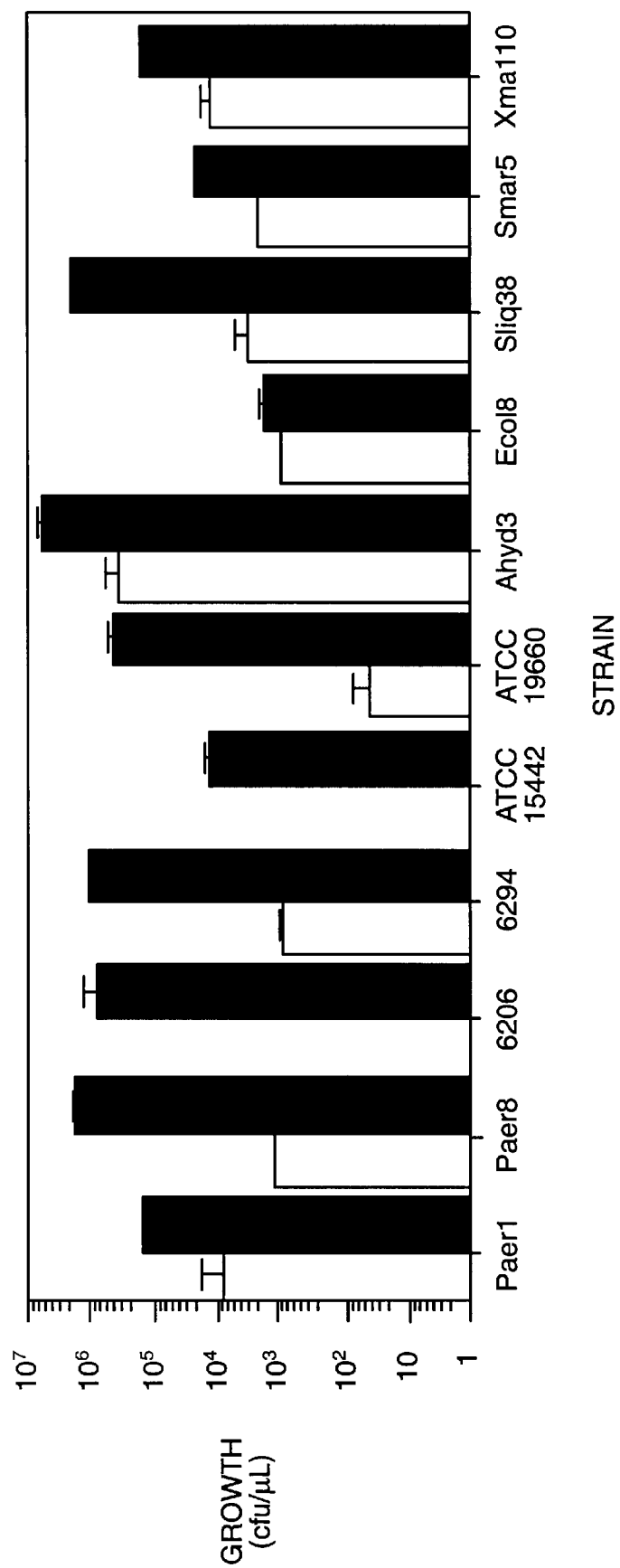
FIG. 1 is a graph depicting the results of testing to determine bacterial growth in lactoferrin.

The present invention provides biomedical devices with an antimicrobial coating and processes for the production of the biomedical devices. It is an unexpected discovery of the invention that certain proteins may be used to provide antimicrobial coatings for biomedical devices. In particular, it is one discovery of the invention that lactoferrin, when used as a surface coating, prevents growth of bacteria adhered to a biomedical device.

In one embodiment, the invention provides a device comprising, consisting essentially of, and consisting of a biomedical device at least one surface of which comprises, consists essentially of, and consists of lactoferrin. In yet another embodiment, a method for manufacturing biomedical devices comprising, consisting essentially of, and consisting of contacting at least one surface of a biomedical device with a coating effective amount of lactoferrin is provided.

By "biomedical device" is meant any device designed to be used while in or on either or both human tissue or fluid. Examples of such devices include, without limitation, stents, implants, catheters, and ophthalmic lenses. In a preferred embodiment, the biomedical device is an ophthalmic lens including, without limitation, contact or intraocular lenses. More preferably, the device is a contact lens.

Lactoferrin is a protein that occurs naturally in human tears and is the dominant iron-binding protein in mucosal fluids. Lactoferrin functions to limit the amount of extracellular iron available to bacteria. Apart from its iron chelating effect, lactoferrin also is known to destabilize the outer membranes of gram negative bacteria.

Lactoferrin useful in the invention is commercially available, such as human and bovine lactoferrin. Alternatively, synthetic lactoferrin made by known synthesis methods may be used. Preferably, the degree of purity of the lactoferrin used is about 80 percent.

Lactoferrin may be bound to polymer surfaces of a biomedical device by coupling a group in the lactoferrin structure with a group on the polymer. This may be either a direct reaction or a reaction in which a coupling agent reacts to couple the polymer and the lactoferrin. A direct reaction also may be accomplished by the use of a reagent or reaction that activates a group on the polymer or the lactoferrin making it reactive with a functional group on the lactoferrin or polymer without the incorporation of a coupling agent.

For example, one or more amine groups on the lactoferrin may be reacted directly with isothiocyanate, isocyanate, acyl azide, N-hydroxysuccinimide ester, sulfonyl chloride, an aldehyde, glyoxal, epoxide, carbonate, aryl halide, imido ester, or an anhydride group on the polymer. Preferably, carboxyl groups on the polymer surface can be activated for reaction with the amine groups of the lactoferrin using N,N'-carbonyldiimidazole, carbodiimides such as 1-ethyl-3-(3-dimethylaminopropyl) carbodiimide ("EDC"), dicyclohexyl carbodiimide, 1-cyclohexyl-3-(2-morpholinoethyl) carbodiimide, diisopropyl carbodiimide or mixtures thereof. The carbodiimides also may be used with N-hydroxysuccinimide or N-hydroxysulfosuccinimide to form esters that can react with amines to form amides. Other reagents that can be used to promote the reaction of amines with carboxylic acids include N-ethyl-3-phenylisoxazolium-3'-sulfonate and N,N'-carbonyldiimidazole.

Alternatively, amine groups may be coupled to the polymer by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis (succinimidylpropionate), 3,3'-dithiobis (sulfosuccinimidylpropionate), disuccinimidyl suberate, bis (sulfosuccinimidyl) suberate, disuccinimidyl tartarate and the like, imidoesters, including without limitation dimethyl adipimate, difluorobenzene derivatives, including without limitation 1,5-difluoro-2,4-dinitrobenzene, bromofunctional aldehydes, including without limitation gluteraldehyde, and bis epoxides, including without limitation 1,4-butanediol diglycidyl ether. One ordinarily skilled in the art will recognize that other coupling agents may be used depending on the functional groups on the polymer surface.

Any biomedical device having a polymer surface with reactive groups suitable for reacting with the lactoferrin according to the processes of the invention may be used. One ordinarily skilled in the art will recognize that, if the desired polymer surface does not contain suitable reactive groups, reactive groups may be incorporated into the polymer by conventional organic synthesis methods. Alternatively, the reactive groups may be introduced by the addition of polymerizable monomers containing reactive groups into the monomer mixture used to form the polymer.

Examples of useful polymer surfaces are surfaces formed from, without limitation, polymers and copolymers of styrene and substituted styrenes, ethylene, propylene, acrylates and methacrylates, N-vinyl lactams, acrylamides and methacrylamides, acrylonitrile, acrylic and methacrylic acids as well as polyurethanes, polyesters, polydimethylsiloxanes and mixtures thereof. Such polymers may include hydrogels and silicone containing hydrogels. Preferably, lightly crosslinked polymers and copolymers of 2-hydroxyethylmethacrylate ("HEMA") are used. By "lightly crosslinked" is meant that the polymer has a low enough crosslink density so that it is soft and elastic at room temperature. Typically, a lightly crosslinked polymer will have about 0.1 to about 1 crosslinking molecule per about 100 repeating monomer units. Examples of suitable lightly crosslinked HEMA polymers and copolymers include without limitation, ETAFILCON™ and copolymers of glycerol methacrylate and HEMA. Also preferably, silicone hydrogels, especially those of hydrophilic monomers, such as N,N-dimethylacrylamide, are used.

In one embodiment of the process for making the device of the invention, the surface to be coated is contacted with the lactoferrin and at least one coupling agent and/or activating reagent in any convenient manner. For example, the device may be placed in a solution of lactoferrin and solvent into which the coupling agent or activating reagent is added. As an alternative, the device surface may first be treated with the coupling agent or activating reagent and the surface then placed in a lactoferrin solution. As yet another alternative, the lactoferrin may be reacted alone with the polymer surface.

Suitable solvents for use in the invention are those that are capable of dissolving lactoferrin and/or the coupling agent or activating reagent. Preferably, the coating process is carried out in water, alcohol, or mixtures thereof. EDC is effective in aqueous solutions and, thus, is a preferred activating agent.

The coupling agents or activating agents may be used alone or in combination with agents capable of stabilizing any reactive intermediate formed. For example, EDC may be used with N-hydroxysuccinimide as a stabilizer. Additionally, it may be necessary to adjust the solution pH. Preferably, the pH is adjusted to about 2.0 to about 9.0, more preferably about 4.0 to about 7.5.

A coupling effective amount of the coupling agent is used which amount is sufficient to couple the lactoferrin to the device surface. Alternatively, an activating effective amount of the activating reagent is used which amount is sufficient to render the lactoferrin and polymer surface reactive to each other. The precise amount of coupling agent or activating reagent used will depend on the surface's chemistry as well as the agent or reagent selected. Generally, about 0.01 to about 10 weight percent, preferably about 0.01 to about 5.0, more preferably, about 0.01 to about 1 weight percent of coupling agent is used based on the weight of the coating solution. By coating solution is meant the lactoferrin with one or more of the solvent, coupling agent, activating reagent and buffer. Typically, the amount of coating solution used per lens will be about 0.1 ml to about 100 ml, preferably about 0.2 ml to about 80 ml, more preferably about 0.5 ml to about 10 ml per lens is used. If an activating reagent is used, about 0.1 mg to about 100 mg, preferably about 1.0 to about 50 mg per lens of activating reagent is used.

In the processes of the invention, a coating effective amount of lactoferrin is used meaning an amount that when contacted with the surface is sufficient to coat the surface so as to impart the desired antimicrobial properties to the surface. In the case of contact lenses, generally, the amount of lactoferrin contacted with the lens is about 0.1 to about 100 mg, preferably about 2 mg to about 50 mg per lens. The amount of coating resulting per contact lens is about 0.1 to about 1000 µg.

Temperature and pressure are not critical to the processes of the invention and the process may be conveniently carried out at room temperature and pressure. The contact time used will be a length of time sufficient to coat the surface to the extent desired. Preferably, contact time is about 0.5 to about 24 hours.

Following contacting, the surface may be washed with water or buffered saline solution to remove unreacted lactoferrin, coupling agent, activating reagent, solvent, and byproducts. Optionally, the coated surface may be heated in water to extract residual coating, coupling agent, activating reagent, and byproducts and to ensure the break down of any coupling agent-stabilizer complexes that may have formed.

One ordinarily skilled in the art will recognize that the polymer for producing the surface to be coated by the method of the invention may contain other monomers and additives. For example, ultra-violet absorbing monomers, reactive tints, processing aids, and the like may be used.

The invention will be further clarified by a consideration of the following, non-limiting examples.

EXAMPLES

Example 1

All strains were incubated for 18 hours at 35° C., then subcultured into 10 ml of tryptone soya broth (TSB; Oxoid) or, in the case of *Haemophilus influenzae*, 12 ml of cerebrospinal fluid (CSF; Oxoid). Bacteria were grown to stationary phase in batch culture for 18 hours at 35° C. without agitation, subsequently harvested by centrifugation (2060× g) at 25° C., and washed three times in 10 ml phosphate-buffered saline (PBS; 0.137 M NaCl, 2.6 mM KCl, 1.5 mM $KH_2PO_4$, 1.66 mM $Na_2HPO_4$; pH 7.4). After the final wash, the bacteria were re-suspended in PBS; an optical density of 1.0 at 660 nm ($OD_{660}$) equivalent to approximately $1.0\times10^9$ cfu/ml.

TABLE 1

| Strain | Species | Source |
| --- | --- | --- |
| Paer1 | *Pseudomonas aeruginosa* | Contact lens induced acute red eye (CLARE) |
| Paer8 | *P. aeruginosa* | Corneal infiltrates |
| 6206 | *P. aeruginosa* | Bacterial keratitis |
| 6294 | *P. aeruginosa* | Bacterial kerafitis |
| ATCC 15442 | *P. aeruginosa* | Enviromnental |
| ATCC 19660 | *P. aeruginosa* | Septicaemia |
| Ahyd3 | *Aeromonas hydrophila* | CLARE |
| Ecol8 | *Escherichia coli* | CLARE |
| Hinf1 | *Haemophilus influenzae* | CLARE |
| Sliq38 | *Serratia liquefaciens* | CLARE |
| Smar5 | *Serratia marcescens* | CLARE |
| Xmal10 | *Stenotrophomonas maltophilia* | CLARE |

To test the ability of the protein lactoferrin to support bacterial growth, a viability count of bacteria in the presence of lactoferrin was carried out. Bacteria of all twelve strains were grown, harvested, and re-suspended according to the methods given above. Suspensions of bacteria were mixed with human milk lactoferrin to give a final bacterial concentration of $10^3$ cfu/ml and final lactoferrin concentration of 2.5 mg/m in a final volume of 200 µL. The lactoferrin concentration was chosen to approximate the concentration in human tears. For each strain a negative control was also used comprising only bacteria ($10^3$ cfu/μL) in PBS. Solutions were assayed immediately, or incubated at 35° C. with agitation, and assayed at time intervals of 1 hour, 4 hours, and 24 hours. Viable counts were assayed by plating out log serial dilutions of each suspension onto nutrient agar or, in the case of Hinfl, onto chocolate agar to assay viable counts.

The results are presented in FIG. 1. The data demonstrate that lactoferrin did not decrease the growth of bacteria after 24 h incubation, but rather induced an increase in growth for most strains. Values are means±standard deviations (four replicates per strain). The results, presented as cfu/μl, are shown for 24 hours of incubation. Hinfl showed no viable counts after 4 hours in either PBS or lactoferrin, and is omitted from the graph.

Example 2

HEMA-based hydrogel lenses were treated with 2.5 mg/ml colostrum lactoferrin for 18 h at 35° C. After treatment, the amount of lactoferrin adsorbed onto the lens surface was assessed using iodine-125 labeled lactoferrin. The lenses were washed with PBS and the amount of lactoferrin measured using a gamma-counter. Approximately 17 ng of lactoferrin per $mm^2$ of lens surface, or approximately 1 μg/lens, was adsorbed onto the surface.

Three lenses were incubated for 10 min at 35° C. in 500 μl of bacterial suspension, then washed three times in 1 ml PBS. Two methods for measuring bacterial adhesion were used, a total count of bacteria and a count of attached viable bacteria. For total counts, the lenses were stained with crystal violet for 5 min, washed twice in PBS, and examined microscopically. Bacterial numbers in 5 fields per lens were counted and converted to numbers of bacteria/$mm^2$. For viable counts, lenses were macerated in 2 ml PBS and subsequently diluted serially and aliquots plated onto agar plates. After incubation of the plates at 35° C. for 18 h, the number of bacteria/$mm^2$ of lens was calculated. Results for strain Paer1 are shown on Table 2.

TABLE 2

| Treatment | Reduction in Bacterial Growth (%) |
|---|---|
| Lactoferrin Adsorbed Lens | 50 |
| Lens Without Lactoferrin Coating | −7 |

The viable counts on the lactoferrin coated lenses were significantly reduced compared to the total count. This result was unexpected because lactoferrin in solution alone, as shown in Example 1, was not capable of significantly reducing the bacteria recovered.

Example 3

50 mg lactoferrin, bovine colostrum—Sigma, and 20 hydrogel contact lenses in 16.6 ml of deionized water were added to 0.30 g 1-[3-(dimethylarnino)propyl]-3-ethylcarbodiimide hydrochloride ("EDC"). After stirring 21 h at room temperature, the lenses were rinsed with multiple changes of solution over 24 h. Extraction with 4M guanidine hydrochloride removed 3 μg unbound lactoferrin per lens. Hydrolysis with concentrated HCl and subsequent amino acid analysis showed 63 μg bound lactoferrin per lens.

Three lenses were incubated for 10 minutes at 35° C. in 500 μl bacterial suspension, then washed three times in 1 ml PBS. Total count of attached bacteria and a count of attached viable bacteria were carried out as for Example 2. Results for strain Paer1 are shown in Table 3. There was reduced growth after adhesion to contact lenses covalently coated with lactoferrin.

TABLE 3

| Bacterial strain | % reduction in bacterial growth-Non-lactoferrin lenses | % reduction in bacterial growth-lactoferrin lenses |
|---|---|---|
| Paer1 | 0.4 | 98 |

The data showed that covalently bonded lactoferrin had a greater impact on bacterial growth than that previously observed for lactoferrin adsorbed/absorbed to the contact lens surface.

Example 4

*P. aeruiginosa* 6294, *P. aeruginosa* ATCC 15442 and *P. aeruginosa* 6206 were added to contact lenses with covalently attached lactoferrin and assayed as described in Example 2. The results show that these strains also show a reduction in bacterial growth after exposure to lactoferrin covalently linked to the contact lens surface

TABLE 4

| Bacterial strain | % reduction in bacterial growth-lactoferrin lenses |
|---|---|
| 6294 | 98 |
| ATCC 15442 | 95 |
| 6206 | 90 |

These results demonstrate that lactoferrin covalently bound to a hydrogel contact lens is able to prevent the growth of different bacterial strains.

Comparative Example

Chick eye white lysozyme (2.0 mg/ml) and bovine colostrum lactoferrin (2.5 mg/ml) were each adsorbed to different HEMA based hydrogel lenses for 18 h at 35° C. After incubation and washing in PBS three times the lenses were incubated for 10 minutes at 35° C. in 500 μl bacterial suspension, then washed three times in 1 ml PBS. The two methods for measuring bacterial adhesion of Example 2 were used, a total count of attached bacteria and a count of attached viable bacteria. Results for strain Paer1 are shown in Table 5.

TABLE 5

| | % reduction in adhesion | |
|---|---|---|
| Bacteria strain | Lysozyme-coating | Lactoferrin-coating |
| Paer1 | 11% | 50% |

As can be seen in Table 5, lysozyme adsorbed to the contact lens only reduced bacterial adhesion by 11% and this decrease in viability compared to total counts was not statistically significant. On the other hand the lactoferrin adsorbed lens showed a significant reduction in viability after initial adhesion (p<0.05). Thus not all tear proteins, or all amine containing molecules, show significant reduction in the ability of bacteria to grow after initial attachment.

What is claimed is:

1. A process for producing a contact lens comprising the step of binding a coating effective amount of lactoferrin to at least one surface of the lens using a coupling effective amount of a coupling agent or an activating amount of an activating agent, wherein the coupling agent comprises one or more members of the group consisting of N-hydroxysuccinimide esters, imido esters, difluorobenzene derivatives, bromofunctional aldehydes, and bis epoxides, wherein the activating agent comprises one or more members of the group consisting of N,N'-carbonyldiimidazole and carbodiimides.

2. The process of claim 1 wherein the coupling agent comprises one or more members of the group consisting of dithiobis(succinimidyl) propionate, bis(sulfosuccinimidyl) suberate, disuccinimidyl tartarate, dimethyl adipimate, 1,5-difluoro-2,4,-dinitrobenzene, gluteraldehyde, and 1,4-butanedioldiglycidyl ether.

3. The process of claim 1 wherein the activating agent comprises one or more members of the group consisting of N,N'-carbonyldiimidazole, 1-ethyl-3-(3-dimethylaminopropyl) carbodiimide, dicyclohexyl carbodiimide, 1-cyclohexyl-3-(2-morpholinoethyl) carbodiimide, diisopropyl carbodiimide, and N-ethyl-3-phenylisoxazolium-3'-sulfonate.

4. The process of claim 3 wherein the activating agent comprises 1-ethyl-3-(3-dimethylaminopropyl) carbodiimide.

5. The process of claim 1 wherein the coating effective amount of lactoferrin is about 0.1 to about 1000 µg per contact lens.

6. A contact lens made by a process comprising the step of binding a coating effective amount of lactoferrin to at least one surface of the lens using a coupling effective amount of a coupling agent or an activating amount of an activating agent, wherein the coupling agent comprises one or more members of the group consisting of N-hydroxysuccinimide esters, imido esters, difluorobenzene derivatives, bromofunctional aldehydes, and bis eposides, wherein the activating agent comprises one or more members of the group consisting of N,N'-carbonyldiimidazole and carbodiimides.

7. The lens of claim 6 wherein the coupling agent comprises one or more members of the group consisting of dithiobis(succinimidyl) propionate, bis(sulfosuccinimidyl) suberate, disuccinimidyl tartarate, dimethyl adipimate, 1,5-difluoro-2,4,-dinitrobenzene, gluteraldehyde, and 1,4-butanedioldiglycidyl ether.

8. The lens of claim 6 wherein the activating agent comprises one or more members of the group consisting of N,N'-carbonyldiimidazole, 1-ethyl-3-(3-dimethylaminopropyl) carbodiimide, dicyclohexyl carbodiimide, 1-cyclohexyl-3-(2-morpholinoethyl) carbodiimide, diisopropyl carbodiimide, and N-ethyl-3-phenylisoxazolium-3'-sulfonate.

9. The lens of claim 6 wherein the coating effective amount of lactoferrin is about 0.1 to about 1000 µg per contact lens.

10. The lens of claim 6 wherein the activating agent comprises 1-ethyl-3-(3-dimethylaminopropyl) carbodiimide.

* * * * *